(12) United States Patent
Yazawa et al.

(10) Patent No.: US 7,465,753 B2
(45) Date of Patent: Dec. 16, 2008

(54) GLYCOSIDE-CONTAINING LIPOSOME

(75) Inventors: Shin Yazawa, Tokushima (JP); Izumi Takai, Tokyo (JP); Touyou Nishimura, Itano-gun (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/564,356

(22) PCT Filed: Jul. 15, 2004

(86) PCT No.: PCT/JP2004/010103

§ 371 (c)(1),
(2), (4) Date: Jan. 12, 2006

(87) PCT Pub. No.: WO2005/007172

PCT Pub. Date: Jan. 27, 2005

(65) Prior Publication Data
US 2006/0193903 A1 Aug. 31, 2006

(30) Foreign Application Priority Data
Jul. 17, 2003 (JP) ............................. 2003-198476

(51) Int. Cl.
*A61K 31/335* (2006.01)
(52) U.S. Cl. ................................... 514/450
(58) Field of Classification Search ............... 424/450; 514/450
See application file for complete search history.

(56) References Cited

U.S. PATENT DOCUMENTS 5,569,464 A * 10/1996 Endo et al. ................. 424/450
5,849,716 A * 12/1998 Akimoto et al. .............. 514/25

FOREIGN PATENT DOCUMENTS

| JP | 1-93562 | 4/1989 |
|---|---|---|
| JP | 3-279394 | 12/1991 |
| JP | 11-60592 | 3/1999 |
| JP | 2000-191685 | 7/2000 |
| JP | 2000-319200 | 11/2000 |
| JP | 2001-354639 | 12/2001 |
| JP | 2002-503685 | 2/2005 |

OTHER PUBLICATIONS

Sarkar Arun K. et al., Fucosylation of Disaccharide Precursors of Sialy Lewis[x] Inhibit Selectin-mediated Cell Adhesion, The Journal of Biological Chemistry, vol. 272, No. 41, pp. 25608-25616, 1997.

Stewart Robert J. et al, A Carbohydrate-Carbohydrate Interaction between Galactosylceramide-Containing Liposomes and Cerebroside Sulfate-Containing Liposomes: Dependence on the Glycolipid Ceramide Composition, Biochemistry, vol. 32, pp. 10666 to 10674, 1993 (English abstract only).

* cited by examiner

*Primary Examiner*—Elli Peselev
(74) *Attorney, Agent, or Firm*—Oblon, Spivak, McClelland, Maier & Neustadt, P.C.

(57) ABSTRACT

A drug product which can maximize the effect of a cholestanol glycoside useful as an anticancer agent. The present invention provides a liposomal composition containing a glycoside exhibiting antitumor activity, a phospholipid, and a positive-charge-providing substance; the glycoside being composed of GlcNAc-Gal-, GlcNAc-Gal-Glc-, Fuc-Gal-, Gal-Glc-, or Gal- as a sugar moiety, and a hydrophobic compound capable of forming a liposome.

8 Claims, 8 Drawing Sheets

[Fig. 1]
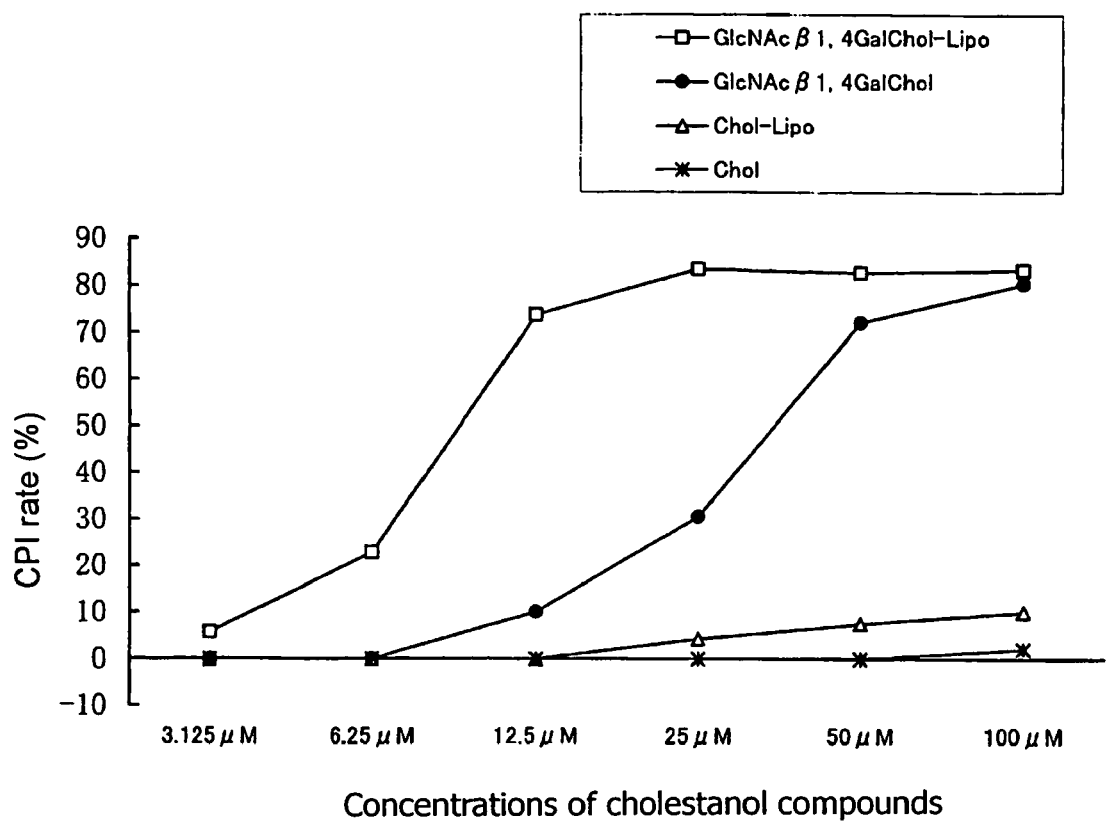

[Fig. 2]
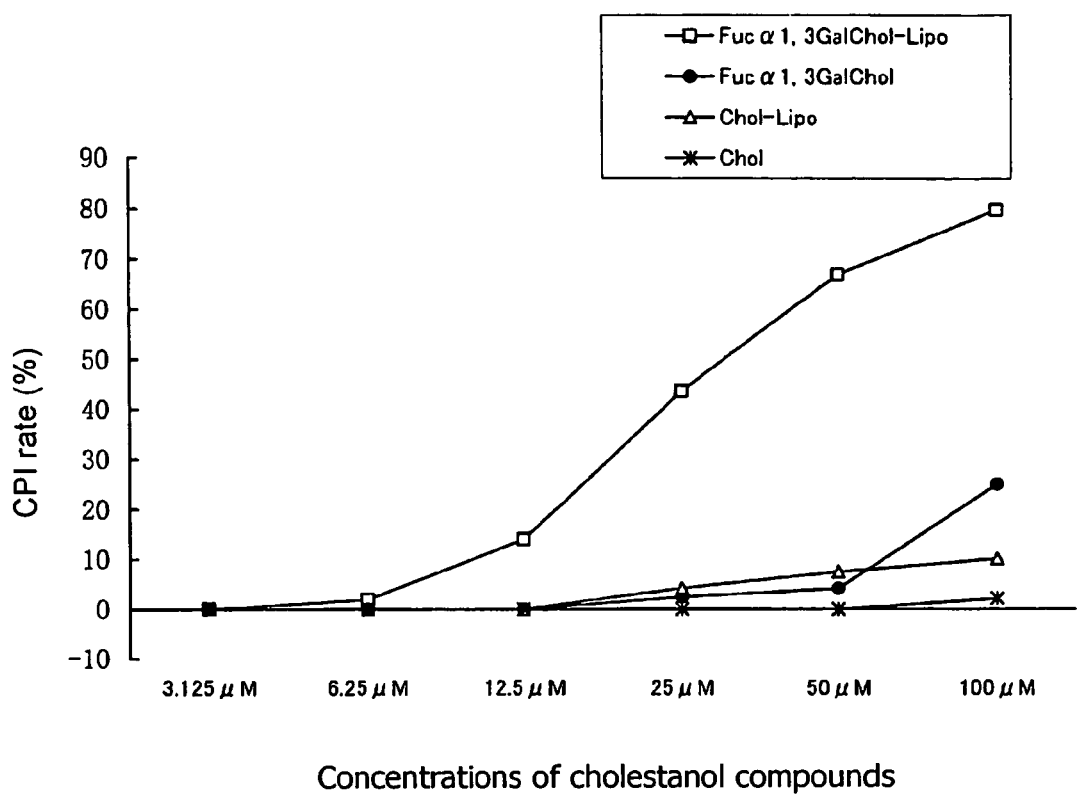

[Fig. 3]
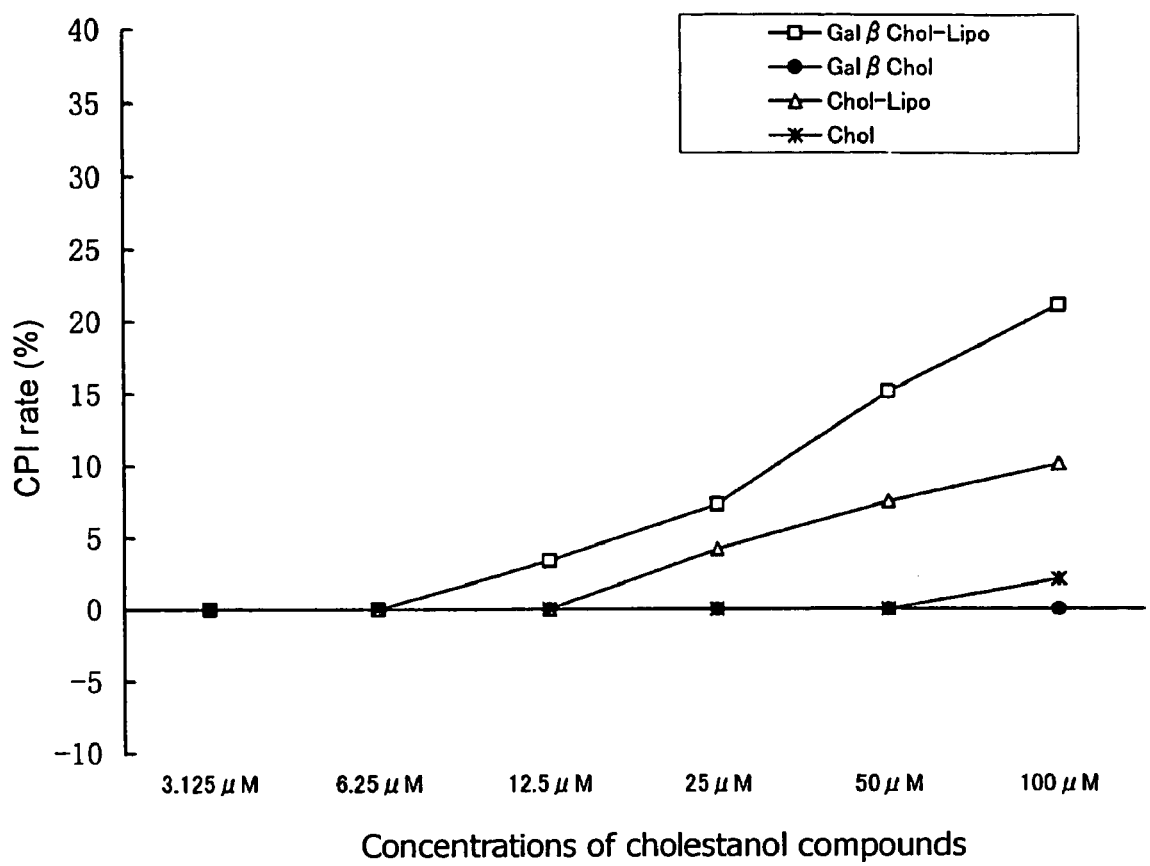

[Fig. 4]
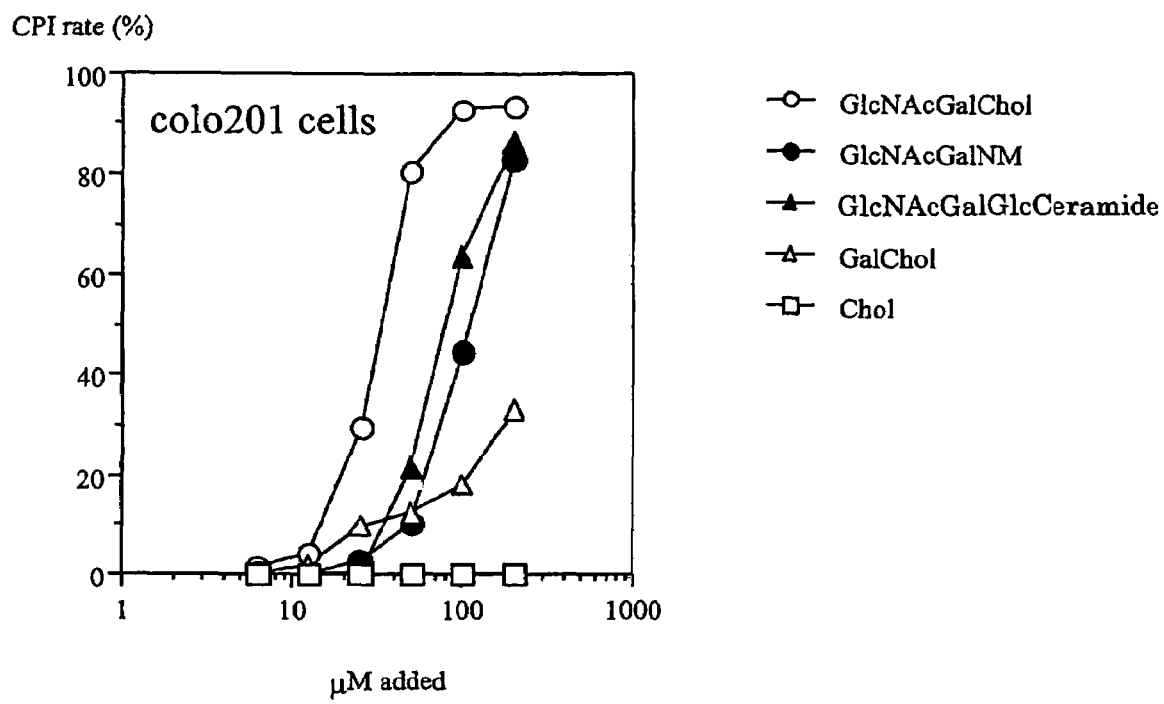

[Fig. 5]
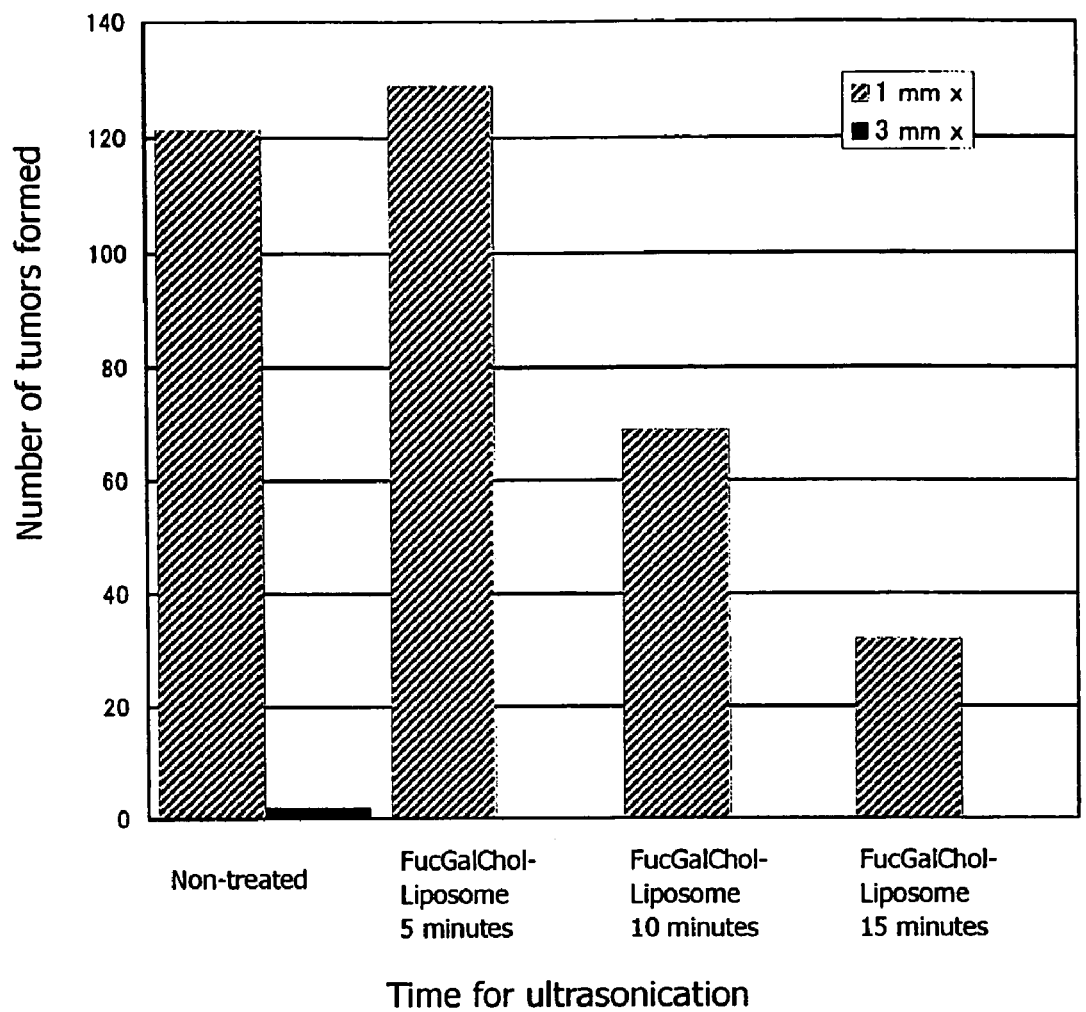

[Fig. 6]
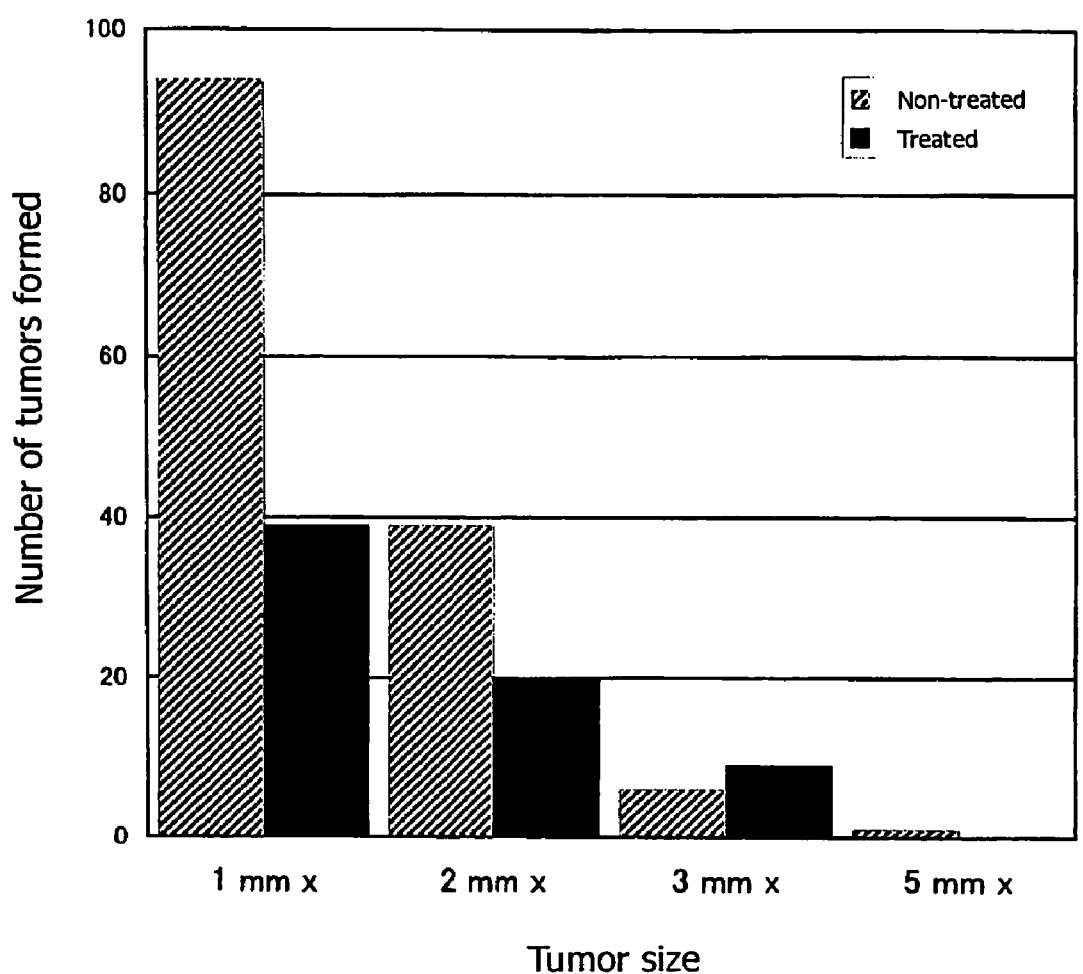

[Fig. 7]
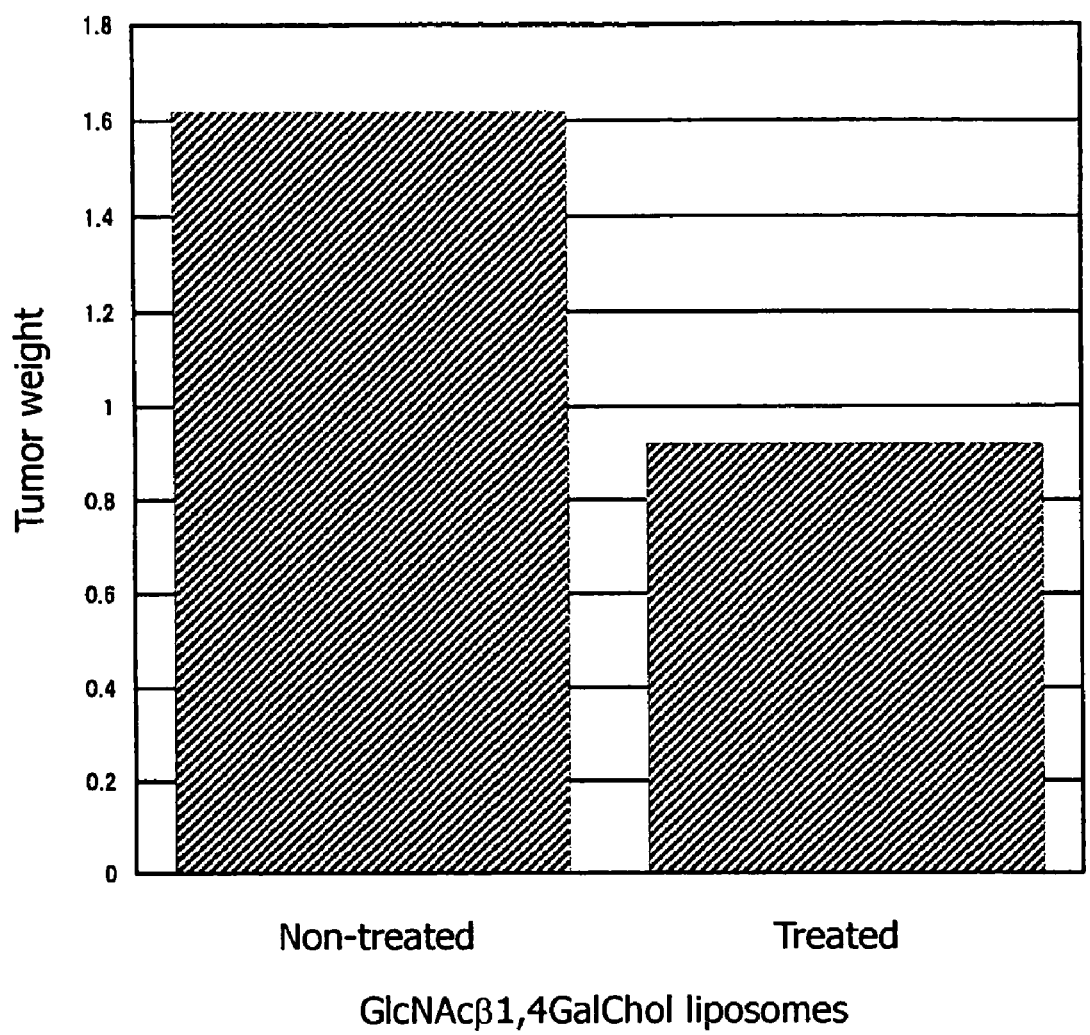
GlcNAcβ1,4GalChol liposomes

[Fig. 8]
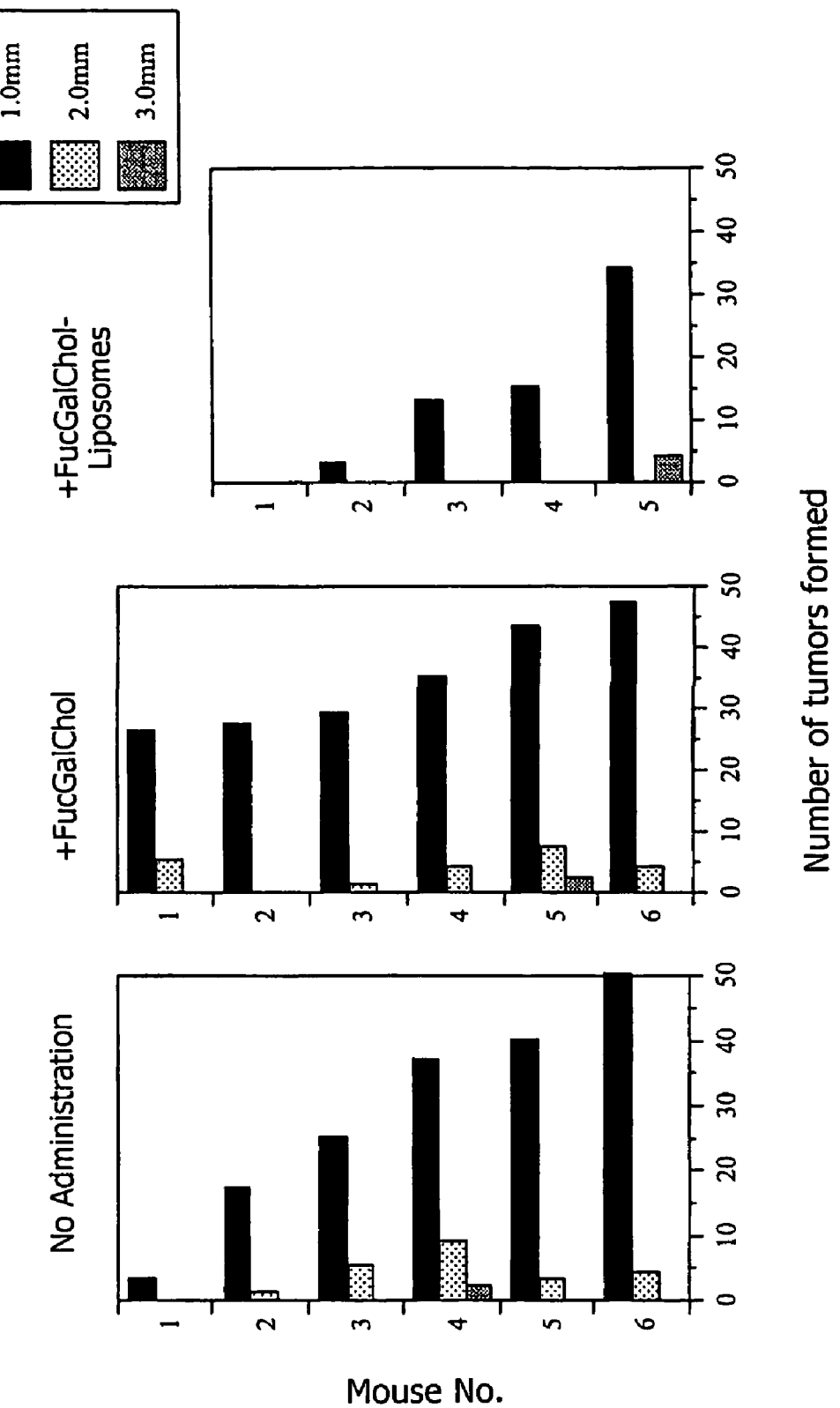

GLYCOSIDE-CONTAINING LIPOSOME

CROSS-REFERENCE TO RELATED APPLICATIONS

The present application is a 35 U.S.C. § 371 National Stage patent application of International patent application PCT/JP04/10103, filed on Jul. 15, 2004, which claims priority to Japanese patent application JP2003-198476, filed on Jul. 13, 2003.

TECHNICAL FIELD

The present invention relates to a liposome (hereinafter may be referred to as a "liposomal composition") containing a glycoside which is useful as an anticancer agent.

BACKGROUND ART

Among other cholestanol glycosides, the below-described cholestanol glycoside (1), which is obtained through bonding of a specific sugar chain to cholestanol formed through saturation of the carbon-carbon double bond of the B ring of cholesterol, exhibits the effect of inhibiting growth of cancer cells, and is a compound useful as an anticancer agent (see Patent Documents 1 and 2).

[F1]

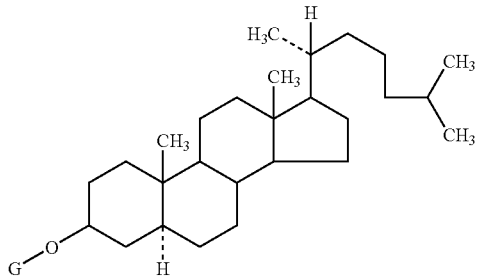

(1)

[wherein G represents GlcNAc-Gal-, GlcNAc-Gal-Glc-, Fuc-Gal-, Gal-Glc-, or Gal-].

A hydrophobic compound such as cholestanol has affinity to cell membranes, and is readily taken into cells. Therefore, a glycoside of such a compound has been considered to be readily taken into various cancer cell lines and to exhibit its effects sufficiently. However, such a glycoside is difficult to use due to its low solubility, and may fail to sufficiently exhibit its effects to some carcinomas.

Patent Document 1: JP-A-11-60592
Patent Document 2: JP-A-2000-191685

DISCLOSURE OF THE INVENTION

An object of the present invention is to provide a drug product which contains a glycoside having antitumor activity, and which enables the glycoside to exhibit its inherent antitumor effects more efficiently.

In view of the foregoing, the present inventors have conducted extensive studies on administration forms of a glycoside of a hydrophobic compound (hereinafter may be referred to as a "hydrophobic compound glycoside") having antitumor activity, and as a result have found that when a liposomal composition is prepared from the glycoside together with a membrane component (at least a phospholipid) and a positive-charge-providing substance, the liposomal composition enables use of the glycoside, which has been difficult to use due to its low solubility, and the composition enables the glycoside to more efficiently exhibit its inherent antitumor effects; for example, the composition exhibits potent antitumor activity against such a tumor line that scarcely responds to the antitumor effects of the glycoside when administered as such.

Accordingly, the present invention provides a liposomal composition containing a glycoside exhibiting antitumor activity, a phospholipid, and a positive-charge-providing substance; the glycoside being composed of GlcNAc-Gal-, GlcNAc-Gal-Glc-, Fuc-Gal-, Gal-Glc-, or Gal- as a sugar moiety, and a hydrophobic compound capable of forming a liposome.

The present invention also provides a liposomal composition containing a glycoside selected from among glycosides represented by the following formulas (1) through (3):

[F2]

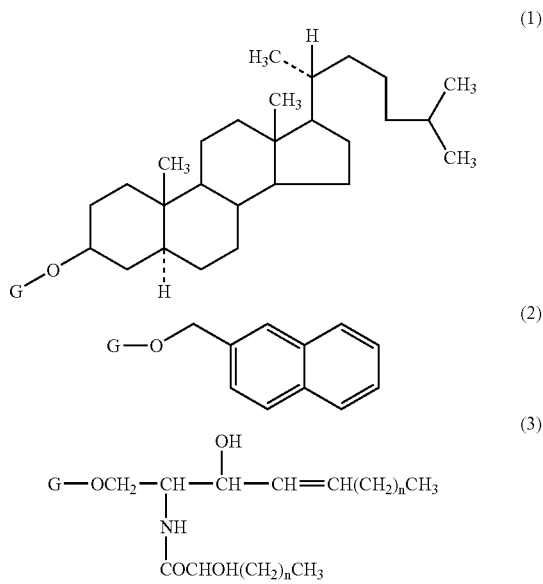

[wherein G represents GlcNAc-Gal-, GlcNAc-Gal-Glc-, Fuc-Gal-, Gal-Glc-, or Gal-, and n represents an integer of 12 to 26]; a phospholipid; and a positive-charge-providing substance.

The present invention also provides an anticancer agent containing the liposomal composition.

According to the present invention, the solubility of a glycoside having antitumor activity is enhanced, and there can be provided a drug product which enables the glycoside to more efficiently exhibit its inherent antitumor effects. Particularly, a drug product containing cholestanol glycoside (1) exhibits potent antitumor activity against such a cancer cell line that scarcely responds to the antitumor effects of the glycoside when administered as such; i.e., the drug product can maximize the antitumor effects of the compound.

BRIEF DESCRIPTION OF THE DRAWINGS

FIG. 1 shows the cancer cell proliferation inhibitory effect of GlcNAcβ1,4GalChol-containing liposomes. In FIG. 1, "-Lipo" represents liposome.

FIG. 2 shows the cancer cell proliferation inhibitory effect of Fucα1,3GalChol-containing liposomes. In FIG. 2, "-Lipo" represents liposome.

FIG. 3 shows the cancer cell proliferation inhibitory effect of GalβChol-containing liposomes. In FIG. 3, "-Lipo" represents liposome.

FIG. 4 shows the cancer cell proliferation inhibitory effect of GlcNAcβ1,3Galβ1,1NM-containing liposomes or GlcNAcβ1,3Galβ1,4Glcβ1,1Ceramide-containing liposomes. In FIG. 4, "-Lipo" represents liposome.

FIG. 5 shows the peritoneal dissemination inhibitory effect of Fucα1,3GalChol-containing liposomes having different particle sizes.

FIG. 6 shows the peritoneal dissemination inhibitory effect of GlcNAcβ1,4GalChol-containing liposomes, particularly shows the results of counting the number of tumors formed.

FIG. 7 shows the peritoneal dissemination inhibitory effect of GlcNAcβ1,4GalChol-containing liposomes, particularly shows the results of measuring tumor weight (g).

FIG. 8 shows comparison in peritoneal dissemination inhibitory effect between administration of FucGalChol-containing liposomes and administration of FucGalChol alone, particularly shows the results of counting the number of tumors formed.

BEST MODE FOR CARRYING OUT THE INVENTION

The glycoside contained in the liposomal composition of the present invention includes, as a sugar moiety, GlcNAc-Gal-, GlcNAc-Gal-Glc-, Fuc-Gal-, Gal-Glc-, or Gal-, includes, as an aglycon, a hydrophobic compound capable of forming liposomes, and has antitumor activity.

Examples of the hydrophobic compound capable of forming liposomes include biocomponents such as cholesterol, ceramide, hydrophobic amino acids, fatty acids (e.g., oleic acid, linoleic acid, and linolenic acid), and fat-soluble vitamins; compounds having an aromatic ring, such as naphthalene derivatives (e.g., naphthalene methanol); and cholesterol derivatives (e.g., cholestanol). Of these, ceramide, naphthalene derivatives, and cholesterol derivatives are preferred, with cholestanol, which is formed through saturation of the carbon-carbon double bond of the B ring of cholesterol, being particularly preferred.

When the sugar moiety is GlcNAc-Gal-, GlcNAcβ1,3-Galβ- or GlcNAcβ1,4-Galβ- is preferred. When the sugar moiety is GlcNAc-Gal-Glc-, GlcNAcβ1,3-Galβ1,4-Glc- is preferred. When the sugar moiety is Fuc-Gal-, Fucα1,3Gal- is preferred. When the sugar moiety is Gal-Glc-, Galβ1,4Glcβ- is preferred. When the sugar moiety is Gal-, Galβ- is preferred.

Preferred examples of the glycoside include the following cholestanaol glycoside (1), naphalente methanol glycoside (2), and ceramide glycoside (3):

[F3]

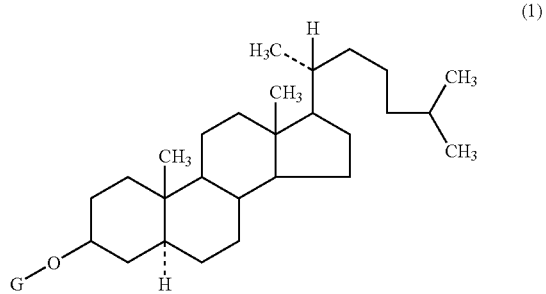
(1)

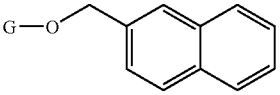

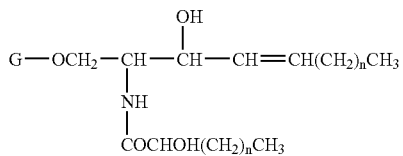

[wherein G represents GlcNAc-Gal-, GlcNAc-Gal-Glc-, Fuc-Gal-, Gal-Glc-, or Gal-, and n represents an integer of 12 to 26].

Of these, cholestanol glycoside (1) is particularly preferred, from the viewpoint of anticancer effects. Preferred examples of the glycoside represented by formula (1) include the following compounds:

G=GlcNAc-Gal- (1)

3-β-cholestanyl 3-O-(2-acetamido-2-deoxy-β-D-glucopyranosyl)-β-D-galactopyranoside, and 3-β-cholestanyl 4-O-(2-acetamido-2-deoxy-β-D-glucopyranosyl)-β-D-galactopyranoside;

G=GlcNAc-Gal-Glc- (2)

3-β-cholestanyl 4-O-{3-O-(2-acetamido-2-deoxy-β-D-glucopyranosyl)-β-D-galactopyranosyl}-β-D-glucopyranoside;

G=Fuc-Gal- (3)

3-β-cholestanyl 3-O-(α-L-fucopyranosyl)-β-D-galactopyranoside;

G=Gal-Glc- (4)

3-β-cholestanyl 4-O-(β-D-galactopyranosyl)-β-D-glucopyranoside; and

G=Gal- (5)

3-β-cholestanyl β-D-galactopyranoside.

The glycoside employed in the present invention can be extracted from a living organism, or produced through known chemical reaction. Alternatively, the glycoside can be obtained through combination of such extraction and reaction. For example, the aforementioned cholestanol glycoside (1) can be produced through the method described in JP-A-11-60592 or JP-A-2000-191685; the naphthalene methanol glycoside (2) can be produced through the method described in J. Biol. Chem. 272 (41) 25608, 1997; and the ceramide glycoside (3) can be extracted from, for example, human erythrocytes, liver, gastrointestinal mucosa, or meconium.

The glycoside has antitumor activity. As used herein, the expression "the glycoside has antitumor activity" refers to the case where, in vivo, the glycoside exhibits antitumor effects against at least one carcinoma, or where, in vitro, the glycoside has activity to inhibit or suppress growth of at least one cancer cell line.

The amount of the glycoside contained in the liposomal composition of the present invention is 0.3 to 2.0 mol, preferably 0.8 to 1.5 mol, on the basis of 1 mol of a phospholipid.

The liposomal composition of the present invention contains at least a phospholipid as a membrane component.

Examples of the phospholipid include phosphatidylcholines such as dilauroylphosphatidylcholine, dimyristoylphosphatidylcholine, dipalmitoylphosphatidylcholine, distearoylphosphatidylcholine, dioleoylphosphatidylcholine, dilinoleoylphosphatidylcholine, myristoylpalmitoylphosphatidylcholine, myristoylstearoylphosphatidylcholine, and palmitoylarachidoylphosphatidylcholine; phosphatidylethanolamine; phosphatidylserine; phosphatidylinositol; and phosphatidic acid. The phospholipid may be a naturally occurring product, or may be obtained through semisynthesis or total synthesis. The phospholipid may be a processed phospholipid such as a hydrogenated phospholipid. These phospholipids may be employed singly or in combination of two or more species.

Of the aforementioned phospholipids, phosphatidylcholines are preferably employed, and 1α-dipalmitoylphosphatidylcholine (DPPC) is particularly preferably employed, since electrically neutral, stable liposomes can be formed.

The positive-charge-providing substance is added for positively charging the surface of a lipid membrane. When the surface of liposomes is positively charged, the liposomes are expected to come into natural contact with cells having negatively charged membrane surfaces.

Examples of the positive-charge-providing substance include aliphatic amines such as stearylamine and oleylamine; and aromatic amines such as fluoreneethylamine. Of these, aliphatic amines are preferred, and stearylamine is particularly preferably employed.

The amount of the positive-charge-providing substance contained in the liposomal composition is 0.04 to 0.15 mol, preferably 0.1 to 0.15 mol, on the basis of 1 mol of the phospholipid.

If desired, the liposomal composition of the present invention may contain, in addition to the aforementioned components, a membrane structure stabilizer such as cholesterol, a fatty acid, or diacetyl phosphate.

The aqueous solution employed for dispersing the membrane component is preferably water, saline, a buffer, an aqueous solution of a sugar, or a mixture thereof. The buffer to be employed is preferably an organic or inorganic buffer which has buffering action in the vicinity of the hydrogen ion concentration of body fluids. For example, a phosphate buffer can be employed.

No particular limitation is imposed on the method for preparing the liposomal composition of the present invention, and the composition can be prepared through a customary method. For example, the liposomal composition can be prepared through the method described in JP-A-57-82310, JP-A-60-12127, JP-A-60-58915, JP-A-1-117824, JP-A-1-167218, JP-A-4-29925, or JP-A-9-87168, the method described in Methods of Biochemical Analysis (1988) 33, p 337, or the method described in "Liposome" (Nankodo).

Next will be described preparation of the liposomal composition of the present invention through the method described in Japanese Patent Application Laid-Open (kokai) No. 9-87168.

Firstly, an organic solvent and water are added to and mixed with a glycoside, a phospholipid, and a positive-charge-providing substance, and subsequently the organic solvent is completely removed by means of a rotary evaporator or a similar apparatus, followed by removal of the water. In this case, the mixing proportions of the membrane component, the positive-charge-providing substance, and the glycoside may be, for example, 52:8:20 (by mole). However, so long as the mixing proportions fall within a range nearly equal to the above range, particular problems do not arise. When the mixing proportion of the glycoside is low, if desired, a membrane structure stabilizer such as cholesterol may be added. However, when the mixing proportion of the glycoside is high, addition of such a membrane structure stabilizer is not necessarily required.

No particular limitation is imposed on the organic solvent to be employed, so long as it is a volatile organic solvent which is insoluble in water. Examples of the organic solvent which may be employed include chloroform, chloromethane, benzene, and hexane. In consideration of solubility, an organic solvent having relatively high polarity (e.g., ethanol or methanol) may be appropriately added to such a water-insoluble solvent, and the thus-prepared organic solvent mixture may be employed. No particular limitation is imposed on the mixing proportions of the organic solvent mixture and water, so long as a uniform solvent mixture is obtained.

In the case where water is added for preparation of the liposomal composition, removal of the water is generally carried out through freeze-drying. However, removal of the water is not necessarily performed through freeze-drying, and may be performed through drying in a reduced-pressure desiccator. After removal of the water, the aforementioned aqueous solution for dispersion is added, followed by impregnation by means of, for example, a Vortex mixer, to thereby form the liposomal composition.

The particle size of the liposomal composition of the present invention is preferably 10 μm or less, more preferably 3 μm or less, from the viewpoint of tumor-suppressive effect.

Liposomes having a uniform particle size can be prepared through, for example, ultrasonic treatment, extrusion treatment by use of a porous membrane filter, treatment by use of a high-pressure injection emulsifier, or combination of such treatments. Smaller liposome particles can be prepared by, for example, performing ultrasonic treatment for a long period of time.

The thus-prepared liposomal composition of the present invention exhibits very excellent effect of inhibiting growth of cancer cells, as described below in Examples. Particularly when the cholestanol glycoside (1) is employed, the liposomal composition exhibits potent antitumor activity against such a cancer cell line that scarcely responds to the antitumor effects of the glycoside when administered as such. In general, liposomes are vesicles formed of phospholipid bilayer membranes, and liposomes encapsulating a drug are prepared for the purpose of bringing the drug into cells when they are dispersed and fused with the cell membranes. Accordingly, the properties of the drug have been considered unchanged through formation of liposomes from the drug. Therefore, it is quite surprising that the antitumor activity of the cholestanol glycoside is drastically enhanced through formation of a liposomal composition from the cholestanol glycoside.

Thus, a drug product containing the liposomal composition is useful as an anticancer agent which enables the glycoside to more efficiently exhibit its inherent antitumor effects.

The product form of the anticancer agent of the present invention can be appropriately determined depending on the treatment site or the therapeutic purpose. So long as an additive which impedes the stability of the form of the liposomal composition is not employed, the anticancer agent can be prepared through a known preparation method into, for example, a peroral product, an injection, a suppository, an ointment, or a patch.

A peroral solid product (e.g., a tablet, a coated tablet, a granule, a powder, or a capsule) can be prepared by adding, to the liposomal composition of the present invention, an excipient and, if desired, other additives such as a binder, a disintegrating agent, a lubricant, a coloring agent, a flavoring agent, and a deodorant, followed by customary processing. The additive to be employed may be an additive which is generally used in the art. Examples of the excipient include lactose, sucrose, sodium chloride, glucose, starch, calcium carbonate, kaolin, microcrystalline cellulose, and silicic acid. Examples of the binder include water, ethanol, propanol, simple syrup, liquid glucose, liquid starch, liquid gelatin, carboxymethyl cellulose, hydroxypropyl cellulose, hydroxypropyl starch, methyl cellulose, ethyl cellulose, shellac, calcium phosphate, and polyvinyl pyrrolidone. Examples of the disintegrating agent include dry starch, sodium alginate, agar powder, sodium hydrogencarbonate, calcium carbonate, sodium lauryl sulfate, monoglyceride stearate, and lactose. Examples of the lubricant include purified talc, stearic acid salts, borax, and polyethylene glycol. Examples of the flavoring agent include sucrose, orange peel, citric acid, and tartaric acid.

A peroral liquid product (a peroral solution, a syrup, or an elixir) can be prepared by adding, to the liposomal composition of the present invention, a flavoring agent, a buffer, a stabilizer, a deodorant, or the like, followed by customary processing. The flavoring agent to be employed for this preparation may be the aforementioned one. Examples of the buffer include sodium citrate. Examples of the stabilizer include tragacanth, gum arabi, and gelatin.

An injection (e.g., a subcutaneous injection, an intramuscular injection, or an intravenous injection) can be prepared by adding, to the liposomal composition of the present invention, a pH-adjusting agent, a buffer, a stabilizer, an isotonicity-imparting agent, a local anesthetic agent, or the like, followed by customary processing. Examples of the pH-adjusting agent and the buffer employed for this preparation include sodium citrate, sodium acetate, and sodium phosphate. Examples of the stabilizer include sodium pyrosulfite, EDTA, thioglycolic acid, and thiolactic acid. Examples of the local anesthetic agent include procaine hydrochloride and lidocaine hydrochloride. Examples of the isotonicity-imparting agent include sodium chloride and glucose.

A suppository can be prepared by adding, to the liposomal composition of the present invention, a known carrier for drug preparation, such as polyethylene glycol, lanolin, cocoa butter, or fatty acid triglyceride, and, if desired, a surfactant such as Tween (registered trademark), followed by customary processing.

An ointment can be prepared by mixing the liposomal composition of the present invention with, if desired, a commonly employed additive such as a base, a stabilizer, a humectant, or a preservative through a customary technique. Examples of the base include liquid paraffin, white petrolatum, white beeswax, octyldodecyl alcohol, and paraffin. Examples of the preservative include methyl p-hydroxybenzoate, ethyl p-hydroxybenzoate, and propyl p-hydroxybenzoate.

A patch can be prepared in a routine manner by applying, to a commonly employed support, the aforementioned ointment, a cream, a gel, a paste, or the like. Examples of appropriate supports include woven fabrics and non-woven fabrics formed of cotton, staple fiber, and chemical fiber; and films and foam sheets formed of soft vinyl chloride, polyethylene, and polyurethane.

The dose of the anticancer agent of the present invention varies depending on the symptom, body weight, age, sex, etc. of a patient in need thereof. The daily dose of the anticancer agent for an adult is typically about 0.01 to about 200 mg/Kg, preferably 0.1 to 50 mg/Kg, as reduced to the cholestanol glycoside (1). Preferably, the daily dose is administered once a day, or in a divided manner (2 to 4 times a day).

EXAMPLES

The present invention will next be described in more detail by way of Examples.

Example 1

Formation of Liposomes from Cholestanol Glycoside

There were employed, as cholestanol glycosides, "GlcNAcβ1,4GalChol"; i.e., a cholestanol compound of formula (1) in which G is GlcNAcβ1,4Gal, "Fucα1,3GalChol"; i.e., a cholestanol compound of formula (1) in which G is Fucα1,3Gal, and "GalβChol"; i.e., a cholestanol compound of formula (1) in which G is Galβ. For comparison, "Chol"; i.e., a cholestanol compound of formula (1) in which G is H was employed. A 20 μmol/mL solution of each of these compounds (dissolved in chloroform/methanol=5/1 (v/v)) was employed as a starting material.

1α-Dipalmitoylphosphatidylcholine, stearylamine, and each of the aforementioned cholestanol compounds were mixed in proportions of 52/8/20 (by mole) so as to attain a total amount of 700 μL, and subsequently an organic solvent (chloroform/methanol=2/1 (v/v)) (300 μL) and distilled water (1 mL) were added to and mixed with the resultant mixture. Thereafter, the organic solvent was completely removed by means of a rotary evaporator, and the resultant product was subjected to freeze-drying, to thereby completely remove the water. The freeze-dried product was dissolved in PBS (1 mL), followed by ultrasonic treatment (15 W, 15 minutes), to thereby form liposomes having a uniform particle size of about 2 to about 4 μm. The thus-formed liposomes were employed in Examples 2 and 3.

Example 2

Formation of Liposomes from Naphthalene Methanol Glycoside

There was employed, as a naphthalene methanol glycoside, "GlcNAcβ1,4Galβ1,1NM" (NM: naphthalene methanol); i.e., a compound of formula (2) in which G is GlcNacβ1,4-Galβ1,1-, and liposomes were formed from this naphthalene methanol glycoside under conditions similar to those for formation of the cholestanol glycoside liposomes.

Example 3

Formation of Liposomes from Ceramide Glycoside

There was employed, as a ceramide glycoside, "GlcNAcβ1,3Galβ1,4Glcβ1,1Ceramide"; i.e., a compound of formula (3) in which G is GlcNacβ1,3-Galβ1,4-Glc-, and liposomes were formed from this ceramide glycoside in a manner similar to that of formation of the cholestanol glycoside liposomes. In the case of formation of ceramide glycoside liposomes, cholesterol was added as a stabilizer.

Example 4

Cell Proliferation Inhibitory Effect of Cholestanol Glycoside Liposomes

A cultured cancer cell line (colon26 wild) was inoculated into a 96-well plate ($1\times10^4$ cells/100 μL/well), and subsequently a cholestanol glycoside (GlcNAcβ1,4GalChol, Fucα1,3GalChol, GalβChol, or Chol) or each type of the cholestanol glycoside liposomes formed in Example 1 was added to the 96-well plate, followed by incubation at 37° C. for three days. Thereafter, the MTT assay was performed, and the number of live cells was determined. The cell proliferation inhibition rate was obtained by use of the following formula.

Cell proliferation inhibition rate(CPI rate)(%)=(1−OD of treated cells/OD of non-treated cells)×100

As a result, Fucα1,3GalChol, which scarcely exhibits cell proliferation inhibitory effect when employed alone, exhibited remarkable cell proliferation inhibitory effect through formation of liposomes therefrom. Meanwhile, GlcNAcβ1,4GalChol, which has conventionally been shown to have cell proliferation inhibitory effect, was found to exhibit further enhanced cell proliferation inhibitory effect through formation of liposomes therefrom (FIGS. 1, 2, and 3).

Example 5

Cell Proliferation Inhibitory Effect of Naphthalene Methanol Glycoside Liposomes and Ceramide Glycoside Liposomes A cultured cancer cell line (colo201) was inoculated into a 96-well plate ($1\times10^4$ cells/100 μL/well), and subsequently the naphthalene methanol glycoside liposomes formed in Example 2 or the ceramide glycoside liposomes formed in Example 3 were added to the 96-well plate, followed by incubation at 37° C. for three days. Thereafter, the MTT assay was performed, and the number of live cells was determined. The cell proliferation inhibition rate was obtained in a manner similar to that of Example 4.

As a result, GlcNAcβ1,3Galβ1NM or GlcNAcβ1,3Galβ1, 4Glcβ1,1Ceramide, which scarcely exhibits cell proliferation inhibitory effect when employed alone due to its insolubility, was found to exhibit remarkable cell proliferation inhibitory effect through formation of liposomes therefrom (FIG. 4).

Example 6

Peritoneal Dissemination Inhibitory Effect of Cholestanol Glycoside Liposomes (1) Effect of the Particle Size of Fucα1,3GalChol Liposomes Balb/c mice (8 weeks old, female) were employed. A cancer cell line (colon26 wild, $5\times10^4$ cells/200 μL) was intraperitoneally administered to each of the animals. Subsequently, 12 hours, 24 hours, and 48 hours after the cancer cell line administration, Fucα1,3GalChol liposomes (2 μmol/100 μL) which had been prepared through ultrasonic treatment (15 W×5, 10, or 15 minutes) were intraperitoneally administered. Ten days later, the number of tumors at the mesentery was counted. Liposomes having a smaller particle size, which were prepared through prolonged ultrasonic treatment, were found to exhibit higher peritoneal dissemination inhibitory effect (FIG. 5).

(2) Peritoneal Dissemination Inhibitory Effect of GlcNAcβ1, 4GalChol Liposomes

Balb/c mice (8 weeks old, female) were employed. A cancer cell line (colon26 wild, $5\times10^4$ cells/200 μL) was intraperitoneally administered to each of the animals. Subsequently, 24 hours and 48 hours after the cancer cell line administration, GlcNAcβ1,4GalChol liposomes (2 μmol/100 μL) which had been prepared through ultrasonic treatment (15 W, 15 minutes) were intraperitoneally administered. Ten days after the liposome administration, the number of tumors at the mesentery was counted, and 21 days after the liposome administration, the weight of tumors formed at the greater omentum and the mesentery was measured. As a result, the administered GlcNAcβ1,4GalChol liposomes were found to exhibit excellent peritoneal dissemination inhibitory effect (FIGS. 6 and 7).

(3) Comparison in Peritoneal Dissemination Inhibitory Effect Between Administration of FucGalChol Liposomes and Administration of FucGalChol Alone Balb/c mice (8 weeks old, female) were employed. A cancer cell line (colon26 wild, $5\times10^4$ cells/200 μL) was intraperitoneally administered to each of the animals. Subsequently, 0, 24, and 48 hours after the cancer cell line administration, FucGalChol liposomes which had been prepared through ultrasonic treatment (15 W, 15 minutes), or FucGalChol was intraperitoneally administered (2 μmol/100 μL). Ten days later, the amount of tumors formed at the mesentery was counted.

As a result, tumor formation was found to be strongly inhibited in an FucGalChol liposome administration group, as compared with the case of a non-treated group or an FucGalChol administration group (FIG. 8).

What is claimed is:

1. A liposomal composition comprising:

a glycoside exhibiting antitumor activity, wherein said glycoside is represented by a compound of formula (1):

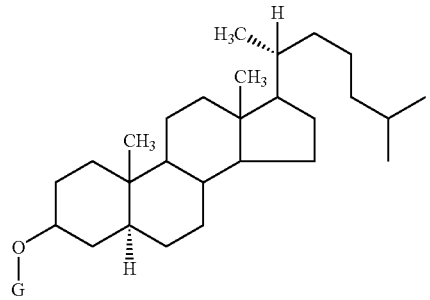

a phospholipid; and a positive-charge-providing aliphatic amine selected from the group consisting of stearylamine and oleylamine, wherein G represents a sugar moiety selected from the group consisting of GlcNAcβ1,4Gal- and Fucα1,3Gal-, and wherein said phospholipid and said positive-charge-providing aliphatic amine are capable of forming a liposome.

2. The liposomal composition according to claim 1, wherein said phospholipid is selected from the group consisting of phosphatidylcholines, phosphatidylethanolamine, phosphatidylserine, phosphatidylinositol, and phosphatidic acid.

3. The liposomal composition according to claim 2, wherein said phospholipid is a phosphatidylcholine selected from the group consisting of dilauroylphosphatidylcholine, dimyristoylphosphatidylcholine, dipalmitoylphosphatidylcholine, distearoylphosphatidylcholine, dioleoylphosphatidylcholine, dilinoleoylphosphatidylcholine, myristoylpalmitoylphosphatidylcholine, myristoylstearoylphosphatidylcholine, and palmitoylarachidoylphosphatidylcholine.

4. The liposomal composition according to claim 3, wherein said phosphatidylcholine is dipalmitoylphosphatidylcholine.

5. An anticancer agent comprising:

the liposomal composition according to claim 1; and one or more pharmaceutically acceptable additives selected from the group consisting of excipients, carriers, binders, disintegrating agents, lubricants, humectants, colorants, flavorants, deodorants, preservatives, stabilizers, pH adjusters, buffers, isotonicity-imparting agents, water, surfactants, and anesthetic agents.

6. The anticancer agent according to claim 5, wherein said anticancer agent is formulated in a dosage form selected from the group consisting of a peroral solid, a peroral liquid, an injection, a suppository, an ointment, and a patch.

7. The liposomal composition according to claim 1, wherein said G represents a GlcNAcβ1,4Gal- sugar moiety.

8. The liposomal composition according to claim 1, wherein said G represents a Fucα1,3Gal- sugar moiety.

* * * * *

UNITED STATES PATENT AND TRADEMARK OFFICE
CERTIFICATE OF CORRECTION

PATENT NO.        : 7,465,753 B2
APPLICATION NO.   : 10/564356
DATED             : December 16, 2008
INVENTOR(S)       : Shin Yazawa et al.

It is certified that error appears in the above-identified patent and that said Letters Patent is hereby corrected as shown below:

Claim 3, line 2, should read:

--wherein said phospholipid is a phosphatidylcholine selected--

Signed and Sealed this

Seventeenth Day of March, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,465,753 B2
APPLICATION NO. : 10/564356
DATED : December 16, 2008
INVENTOR(S) : Shin Yazawa et al.

Page 1 of 1

It is certified that error appears in the above-identified patent and that said Letters Patent is hereby corrected as shown below:

Column 10, Claim 3, line 48, should read:

--wherein said phospholipid is a phosphatidylcholine selected--

This certificate supersedes the Certificate of Correction issued March 17, 2009.

Signed and Sealed this

Seventh Day of April, 2009

JOHN DOLL
*Acting Director of the United States Patent and Trademark Office*